United States Patent
McGinley et al.

(10) Patent No.: US 7,458,977 B2
(45) Date of Patent: Dec. 2, 2008

(54) SURGICAL NAVIGATION INSTRUMENT USEFUL IN MARKING ANATOMICAL STRUCTURES

(75) Inventors: Shawn E. McGinley, Fort Wayne, IN (US); Dean M. J. Acker, Warsaw, IN (US); Kevin S. Cook, Warsaw, IN (US); James E. Grimm, Winona Lake, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 628 days.

(21) Appl. No.: 10/357,959

(22) Filed: Feb. 4, 2003

(65) Prior Publication Data

US 2004/0153062 A1  Aug. 5, 2004

(51) Int. Cl.
*A61B 19/00* (2006.01)
(52) U.S. Cl. ........................... 606/130; 600/426
(58) Field of Classification Search ............ 606/53, 606/86, 96–100, 130; 600/426
See application file for complete search history.

(56) References Cited

U.S. PATENT DOCUMENTS

| | | | |
|---|---|---|---|
| 2,951,482 A | 9/1960 | Sullivan | |
| 3,987,795 A | 10/1976 | Morrison | |
| 4,476,862 A | 10/1984 | Pao | |
| 5,007,936 A | 4/1991 | Woolson | 623/23 |
| 5,037,423 A | 8/1991 | Kenna | |
| 5,230,338 A | 7/1993 | Allen et al. | 128/653 |
| 5,251,127 A | 10/1993 | Raab | 364/413.13 |
| 5,305,203 A | 4/1994 | Raab | 364/413.13 |
| 5,326,376 A | 7/1994 | Warner et al. | 623/23 |
| 5,480,453 A | 1/1996 | Burke | 623/23 |
| 5,551,429 A | 9/1996 | Fitzpatrick et al. | 128/653.1 |

(Continued)

FOREIGN PATENT DOCUMENTS

DE  202 17 014  1/2003

(Continued)

OTHER PUBLICATIONS

VerSys Cemented, Cemented Plus, and Cemented CT Hip Prostheses, Surgical Technique for Primary Hip Arthroplasty, Zimmer Inc., 1997.
VerSys Cemented LD/FX Hip Prosthesis, VerSys Press-Fit Ld/FX Hip Prosthesis Surgical Technique, Zimmer Inc., 1996.
European Search Report issued in related European Application No. 07014866.3 on Oct. 11, 2007.

*Primary Examiner*—Kevin T Truong
*Assistant Examiner*—Victor X Nguyen
(74) *Attorney, Agent, or Firm*—Baker & Daniels LLP

(57) ABSTRACT

A surgical instrument having a grip, a reference structure and an alignment head and method of using. The reference structure has at least one reference element that is registrable in a computer assisted navigation system. The reference element may be a reflective structure for use in an optical tracking system, wire loop for sensing a magnetic field, or other suitable device. The alignment head has a substantially planar alignment surface and may also have a plurality of outwardly extending projections or an electrocautery electrode disposed along an edge of the alignment surface and extending parallel to the alignment surface. The projections may be engaged with an anatomical structure to hold the alignment head in a desired position as the alignment surface is used as a guide to mark the anatomical structure. The disclosed instrument may be used when resecting a femur to prepare the femur to receive the femoral component of a prosthetic hip joint.

20 Claims, 3 Drawing Sheets

U.S. PATENT DOCUMENTS

| | | | | |
|---|---|---|---|---|
| 5,622,170 | A | 4/1997 | Schulz | 128/653.1 |
| 5,682,886 | A | 11/1997 | Delp et al. | 128/653.1 |
| 5,682,890 | A | 11/1997 | Kormos et al. | 128/653.2 |
| 5,732,703 | A | 3/1998 | Kalfas et al. | 128/653.1 |
| 5,772,594 | A | 6/1998 | Barrick | 600/407 |
| 5,848,967 | A * | 12/1998 | Cosman | 600/426 |
| 5,871,018 | A | 2/1999 | Delp et al. | 128/898 |
| 5,904,691 | A | 5/1999 | Barnett et al. | 606/130 |
| 5,913,820 | A | 6/1999 | Bladen et al. | 600/407 |
| 5,921,992 | A | 7/1999 | Costales et al. | 606/130 |
| 5,938,661 | A | 8/1999 | Hahnen | 606/46 |
| 5,995,738 | A | 11/1999 | DiGioia, III et al. | 395/500 |
| 6,002,859 | A | 12/1999 | DiGioia, III et al. | 395/500.32 |
| 6,021,343 | A | 2/2000 | Foley et al. | 600/429 |
| 6,033,415 | A | 3/2000 | Mittelstadt et al. | 606/130 |
| 6,096,044 | A | 8/2000 | Ray, III et al. | |
| 6,096,050 | A | 8/2000 | Audette | 606/130 |
| 6,167,145 | A | 12/2000 | Foley et al. | 382/128 |
| 6,190,395 | B1 | 2/2001 | Williams | 606/130 |
| 6,235,038 | B1 | 5/2001 | Hunter et al. | 606/130 |
| 6,236,875 | B1 | 5/2001 | Bucholz et al. | 600/407 |
| 6,258,097 | B1 * | 7/2001 | Cook et al. | 606/91 |
| 6,285,902 | B1 | 9/2001 | Kienzle, III et al. | 600/427 |
| 6,348,058 | B1 | 2/2002 | Melkent et al. | 606/130 |
| 6,379,302 | B1 | 4/2002 | Kessman et al. | 600/437 |
| 6,381,485 | B1 | 4/2002 | Hunter et al. | 600/407 |
| 6,396,939 | B1 | 5/2002 | Hu et al. | 382/128 |
| 6,402,762 | B2 | 6/2002 | Hunter et al. | 606/130 |
| 6,430,434 | B1 | 8/2002 | Mittelstadt | 600/426 |
| 6,432,064 | B1 | 8/2002 | Hibner et al. | |
| 6,434,507 | B1 | 8/2002 | Clayton et al. | 702/152 |
| 6,450,978 | B1 | 9/2002 | Brosseau et al. | 600/595 |
| 6,470,207 | B1 | 10/2002 | Simon et al. | 600/426 |
| 6,474,341 | B1 | 11/2002 | Hunter et al. | 128/899 |
| 6,477,400 | B1 | 11/2002 | Barrick | 600/426 |
| 6,490,467 | B1 | 12/2002 | Bucholz et al. | 600/407 |
| 6,491,699 | B1 | 12/2002 | Henderson et al. | 606/130 |
| 6,493,573 | B1 | 12/2002 | Martinelli et al. | 600/424 |
| 6,499,488 | B1 | 12/2002 | Hunter et al. | 128/899 |
| 6,725,080 | B2 * | 4/2004 | Melkent et al. | 600/424 |
| 6,915,150 | B2 | 7/2005 | Cinquin et al. | |
| 7,033,360 | B2 | 4/2006 | Cinquin et al. | |
| 2001/0012942 | A1 | 8/2001 | Estes et al. | |
| 2002/0068942 | A1 * | 6/2002 | Neubauer et al. | 606/88 |
| 2005/0251148 | A1 | 11/2005 | Friedrich et al. | |
| 2007/0185498 | A2 | 8/2007 | Lavallee | |

FOREIGN PATENT DOCUMENTS

| | | |
|---|---|---|
| DE | 20217014 | 1/2003 |
| DE | 20217014 U1 | 1/2003 |
| EP | 0 495 488 A | 7/1992 |
| EP | 0495488 A | 7/1992 |
| EP | 0495488 A2 | 7/1992 |
| EP | 1 249 213 A | 10/2002 |
| EP | 1249213 A | 10/2002 |
| EP | 1249213 A2 | 10/2002 |
| FR | 2635675 A1 | 3/1990 |
| JP | 2001355435 | 11/2001 |
| WO | WO 00/67650 | 11/2000 |
| WO | WO0067650 A1 | 11/2000 |
| WO | WO 02/05897 A | 1/2002 |
| WO | WO0205897 A1 | 1/2002 |
| WO | WO 02/32328 A | 4/2002 |
| WO | WO 02/32328 A | 4/2002 |
| WO | WO0232328 A2 | 4/2002 |
| WO | WO 02/36031 A | 5/2002 |
| WO | WO0236031 A1 | 5/2002 |

* cited by examiner

SURGICAL NAVIGATION INSTRUMENT USEFUL IN MARKING ANATOMICAL STRUCTURES

BACKGROUND OF THE INVENTION

1. Field of the Invention

The present invention relates to a navigational tool and, more specifically, a tool which may be used in an orthopedic surgical procedure employing computer assisted navigation.

2. Description of the Related Art

The controlled positioning of surgical instruments is of significant importance in many surgical procedures-and various methods have been developed for properly positioning a surgical instrument. Such methods include the use of both mechanical guides and computer assisted navigational systems. Computer assisted navigational techniques typically involve acquiring preoperative images of the relevant anatomical structures and generating a data base which represents a three dimensional model of the anatomical structures. The relevant surgical instruments typically have a known and fixed geometry which is also defined preoperatively. During the surgical procedure, the position of the instrument being used is registered with the anatomical coordinate system and a graphical display showing the relative positions of the tool and anatomical structure may be computed in real time and displayed for the surgeon to assist the surgeon in properly positioning and manipulating the surgical instrument with respect to the relevant anatomical structure.

In such image guided procedures, a robotic arm may be used to position and control the instrument, or, the surgeon may manually position the instrument and use the display of the relative position of the instrument and anatomical structure to position the instrument. Examples of various computer assisted navigation systems which are known in the art are described in U.S. Pat. Nos. 5,682,886; 5,921,992; 6,096,050; 6,348,058 B1; 6,434,507 B1; 6,450,978 B1; 6,490,467 B1; and 6,491,699 B1 the disclosures of each of these patents is hereby incorporated herein by reference.

SUMMARY OF THE INVENTION

The present invention provides a surgical instrument which may be used with a computer assisted navigation system to facilitate the determination of a desired location on an anatomical structure such as a bone and the marking of the structure with a linear mark. For example, the instrument may be used in the location of a desired resection line on the neck of a femur being prepared to receive the femoral component of a prosthetic hip joint and provide an alignment guide that may be used in the marking of a line on the femoral neck.

The invention comprises, in one form thereof, a surgical instrument for determining a location on an anatomical structure in cooperation with a computer assisted navigation system. The surgical instrument includes a grip portion, at least one reference element disposed on the instrument, and an alignment head. The at least one reference element is registerable in the computer assisted navigation system. The alignment head has a substantially planar alignment surface and a plurality of outwardly extending projections disposed along an edge of the alignment surface and extending parallel to the alignment surface wherein the projections are engageable with the anatomical structure and the alignment surface provides a guide for making a mark on the anatomical structure.

In alternative embodiments, the alignment surface may also include a depression located therein. The instrument may also form a rigid elongate body between the reference structure and the alignment head. The projections may each include a surface disposed substantially co-planar with the alignment surface. The at least one reference element may be removably mounted on the surgical instrument and may include at least three non-linearly positioned reference elements.

The at least one reference element may be an electromagnetic field sensor, a light reflective structure, or other suitable structure.

The invention comprises, in another form thereof, a method of preparing a bone for receiving an orthopedic implant. The method includes providing a surgical instrument with at least one reference element registerable in a computer assisted navigation system and an alignment head which has a substantially planar alignment surface and a plurality of outwardly extending projections disposed along an edge of the alignment surface and extending parallel to the alignment surface. The method also includes registering the position of the instrument relative to the position of the bone in the computer assisted navigation system, displaying an image representing the relative positions of the bone and the instrument, displaying a measurement overlay in the image wherein the measurement overlay is dependent upon the position of the instrument, and moving the instrument relative to the bone to position the measurement overlay in a desired location relative to the bone. The method also includes engaging the instrument with the bone after positioning the measurement overlay in the desired location, marking the bone using the alignment surface as a guide for a mark after engaging the instrument with the bone, and positioning a tool to prepare the bone to receive the implant by aligning the tool with the mark on the bone.

In some embodiments, the step of providing a surgical instrument may include removably mounting the at least one reference element to the instrument and there may be at least three non-linearly positioned reference elements disposed on the instrument. The bone may be a femur and the step of marking the bone may include making a linear mark on the femur proximate the femoral neck.

In other embodiments, the at least one reference element is an electromagnetic field sensor and the step of registering the position of the instrument relative to the position of the bone in the computer assisted navigation system includes sensing the electromagnetic field with the at least one reference element. The reference element may alternatively be a light reflective structure and the step of registering the position of the instrument relative to the position of the bone in the computer assisted navigation system includes sensing light reflected by the at least one reference element.

The invention comprises, in yet another form thereof a surgical instrument that includes a grip portion and an alignment head having a substantially planar alignment surface. An electrocautery electrode is disposed on the alignment head and has a cauterizing edge proximate the alignment surface. The cauterizing edge may be oriented substantially parallel with said alignment surface and the electrocautery electrode may define at least a portion of the alignment surface. The instrument may also have disposed thereon at least one reference element registerable in a computer assisted navigation system and that may take the form of at least three non-linearly positioned reference elements.

The instrument may also include a radio transparent portion extending between the alignment head and the grip portion. The radio transparent portion may be formed out of an electrically insulative material and at least one electrically conductive member in electrical communication with the electrocautery electrode may be at least partially disposed within the radio transparent portion. The at least one electrically conductive member may include a conductive member projecting outwardly from said radio transparent portion or a radio opaque conductive member having a plurality of discontinuities viewable in a fluoroscopic image and disposed at predetermined distances from the alignment surface.

The present invention comprises, in still another form thereof, a surgical instrument that includes a grip portion and an alignment head that has a substantially planar alignment surface and a radio opaque member extending rearwardly from the alignment surface. The radio opaque member has a plurality of discontinuities positioned at predefined distances from the alignment surface whereby the radio opaque member may provide a measurement function when viewing a fluoroscopic image containing the alignment head. The radio opaque member may be at least partially encased in a radio transparent material. The instrument may also have disposed thereon at least one reference element that is registerable in a computer assisted navigation system and that may take the form of at least three non-linearly positioned reference elements.

An advantage of the present invention is that it provides a surgical tool that includes an alignment head having a plurality of projections for engaging an anatomical structure such as a bone adjacent an alignment surface. This allows the alignment head to relatively firmly engage the bone to hold the alignment head in place after locating the head in the desired location and use the alignment surface to align a saw blade and mark the bone by partially cutting the bone.

Another advantage of the present invention is that it provides a surgical tool that includes an alignment guide which can be positioned on an anatomical structure at a desired location and in a desired orientation to provide for the making of a linear mark on the anatomical structure. In contrast, a tool which provides the ability to make only a point mark requires that the instrument be repositioned to mark a second point after making a first point to define a line on the anatomical structure.

Yet another advantage of the present invention is that it provides a surgical tool which may be used in combination with a device which displays an anatomical structure and a measurement overlay which is moved relative to the anatomical structure in the display based upon the actual relative positions of the surgical instrument and the anatomical structure. Such a feature may be advantageously used in the implantation of a prosthetic hip joint. More specifically, such a feature allows the surgical instrument to be positioned at a desired distance from an anatomical landmark, such as the lesser trochanter, on the femur to mark the neck of the femur for resection without requiring the full exposure of the proximal end of the femur to provide for the aligned measurement between the anatomical landmark and the desired resection location.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Figure 1:
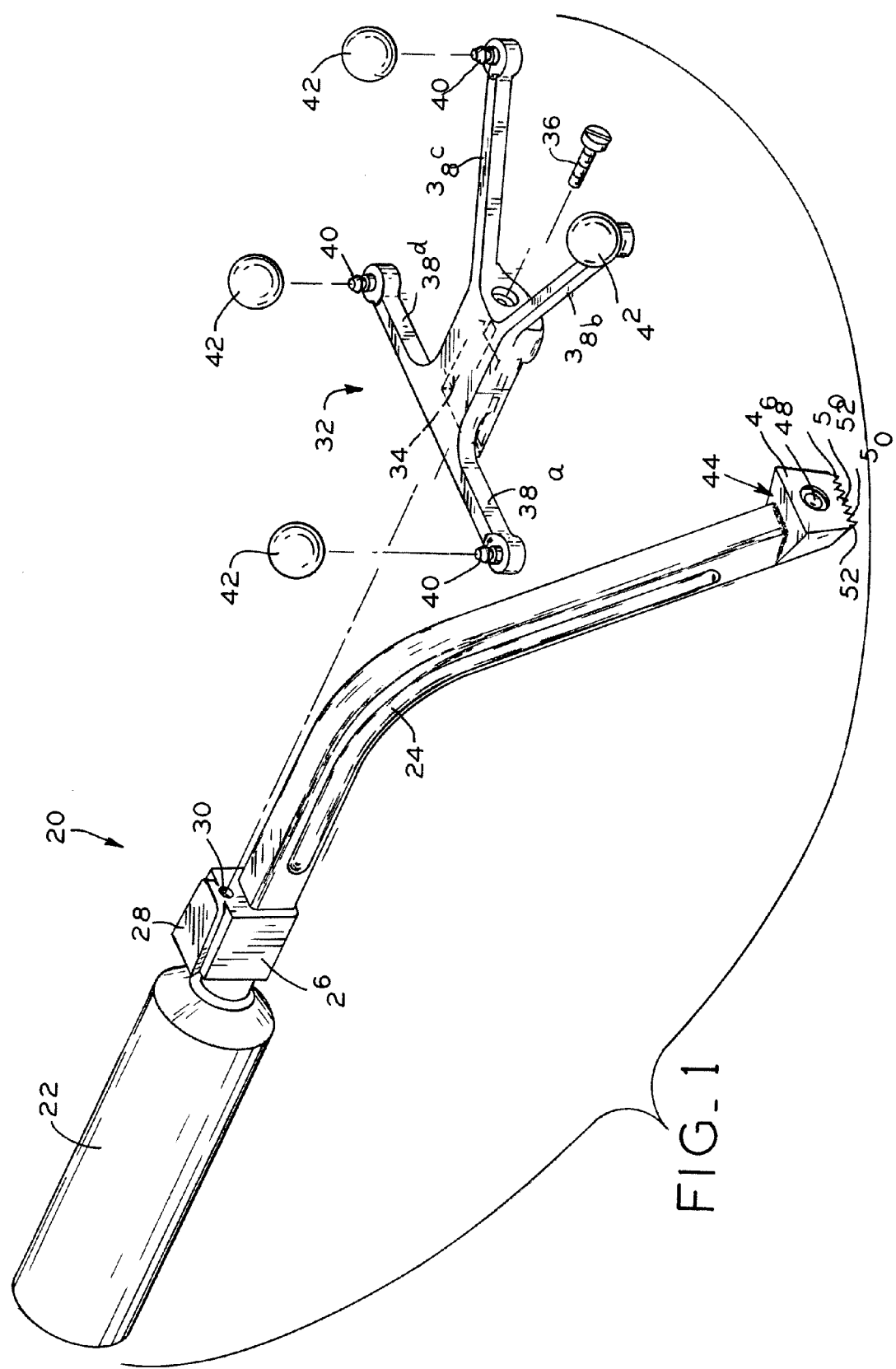
FIG. 1 is an exploded view of a surgical tool in accordance with the present invention.

Corresponding reference characters indicate corresponding parts throughout the several views. Although the exemplification set out herein illustrates an embodiment of the invention, in one form, the embodiment disclosed below is not intended to be exhaustive or to be construed as limiting the scope of the invention to the precise form disclosed.

DESCRIPTION OF THE PRESENT INVENTION

A surgical instrument 20 in accordance with the present invention is shown in FIG. 1. Instrument 20 includes a grip or handle 22 and an elongate neck 24 extending from handle 22. A mounting block 26 is located on neck 24 near handle 22. Mounting block 26 includes a dovetail shaped projection 28 and a threaded aperture 30. Dovetail projection 28 is narrowest proximate aperture 30 and is engageable with a dovetail shaped recess 34 (shown in dashed outline in FIG. 1) on reference structure or array 32. Reference array 32 is mountable on instrument 20 by sliding dovetail recess 34 onto dovetail projection 28. Array 32 is tightly secured to mounting block 26 by engaging threaded fastener 36 with threaded aperture 30 and thereby secures array 32 in a predefined and reproducible relative location on instrument 20. Although reference structure 32 is removably mounted on instrument 20 using a dovetail joint in the illustrated embodiment, alternative methods of securing reference structure in a reproducible orientation may also be employed. Reference structure 32 could also be integrally formed with instrument 20. Array 32 includes four outwardly projecting array arms 38a, 38b, 38c, 38d which each have a mounting post 40 located at their distal end. Reference elements 42 are mounted on mounting posts 40. Spherical elements 42 are reflective structures which are used to reflect light to facilitate the detection and registration of reference elements 42 in a computer assisted navigation system as discussed in greater detail below.

Instrument body 20 may be stainless steel and reference array, excluding reference elements 42, may be aluminum. Alternative materials, however, may also be employed.

Located at the distal end of neck 24 is an alignment head 44. Alignment head 44 includes a substantially planar alignment surface 46 having a depression 48 located therein and a plurality outwardly extending projections 50 located along one edge of alignment surface 46 extending parallel to surface 46. As can be seen in FIG. 1, projections 50 are defined on one side by surfaces 52 which are substantially co-planar with surface 46 and define an extension thereof. Projections 50 may also take alternative forms, for example a series of conical teeth could also be used.

Figure 2:
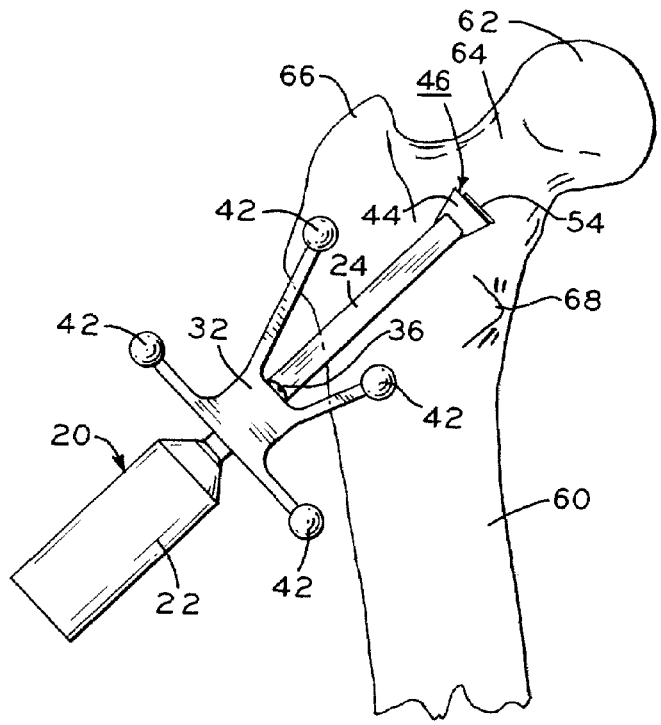
FIG. 2 is a view of the surgical tool of FIG. 1 engaging a femur.

As can be seen in FIG. 2, the serrated edge formed by projections 50 may be directed towards an anatomical structure, such as femur 60, and pressed into engagement therewith. Alignment surface 46 may then be used as a guide to place a mark 54 on femur 60. The use of multiple projections 50 provides a relatively firm engagement between alignment head 44 and femur 60. The firm engagement between alignment head 44 and femur 60 limits the possibility that the position of alignment head 44 will shift relative to femur 60 when using alignment surface 46 as a guide to place a mark 54 on femur 60. A variety of different methods may be employed to mark femur 60 or other bone or anatomical structure. For example, methylene blue or electrocautery may be used to inscribe a line on femur 60. A particularly efficient use of instrument 20 utilizes a conventional surgical saw blade to make mark 54. The saw blade is aligned with surface 46 and femur 60 is marked by partially cutting the bone, after making mark 54 with the saw blade, instrument 20 is removed and the cut completed.

The use of instrument 20 with a femur 60 will now be described. Neck 24 is a rigid elongate body and thus the distance and orientation of alignment head 44 and reference array 32 is constant. The relevant dimensions and relative positions of reference array 32 and alignment head 44 are determined in advance and entered into the computer implemented navigation system so that the position and orientation of alignment head 44, and alignment surface 46 and projections 50 located thereon, may be determined from the position and orientation of reference array 32. Depression 48 located on alignment head 44 may be engaged by a probe having a known geometry and with a reference array mounted thereon. By registering the positions of the reference arrays mounted to instrument 20 and the engaged probe, the position of array 32 relative to alignment head 44 may be confirmed and the computer assisted navigation system calibrated. The relevant dimensional data concerning the anatomical structure which is the subject of the surgical procedure may also be entered into the image guidance system in advance of the surgical procedure.

Figure 3:
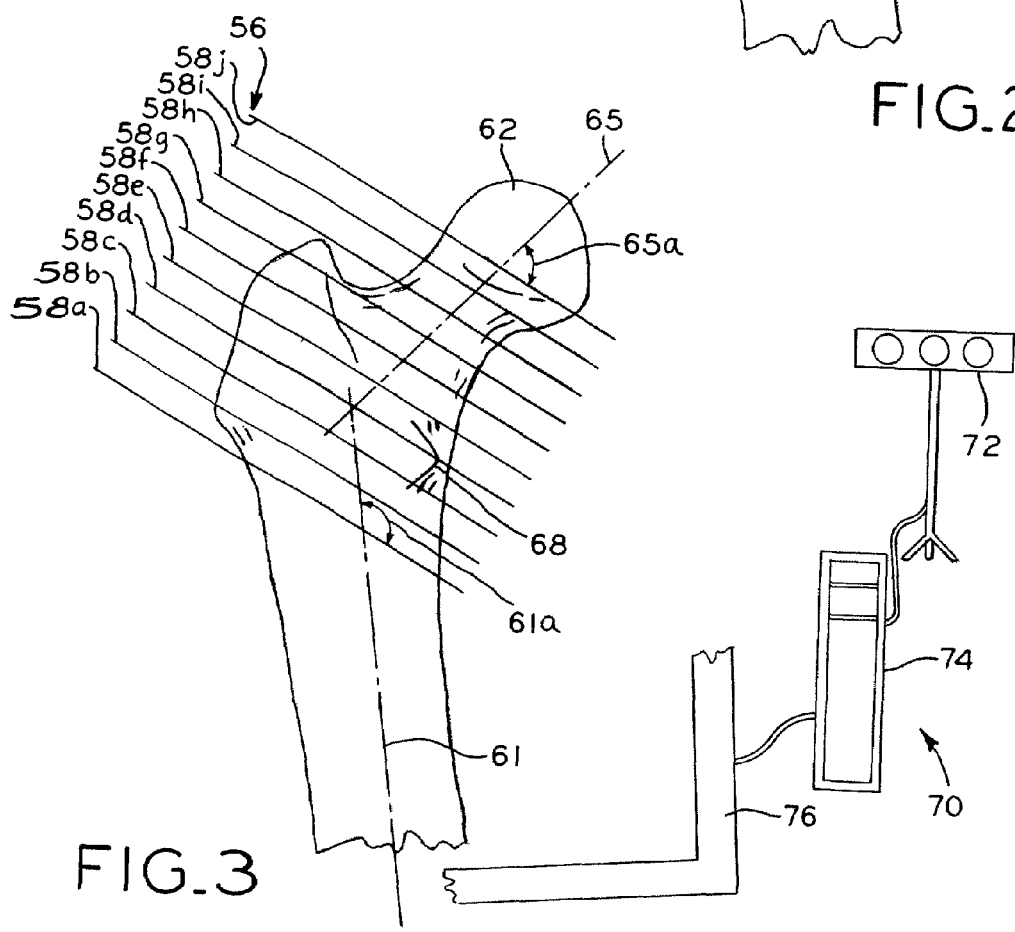
FIG. 3 is a view of a display screen image in accordance with the present invention and a schematic representation of a computer assisted navigation system.

Femur 60 is shown in FIGS. 2 and 3. When implanting a conventional prosthetic hip joint in a patient, the proximal end of the femur must be resected to remove the femoral ball 62 and at least a portion of the femoral neck 64. A femoral component having a stem and a prosthetic femoral ball is subsequently implanted on the femur. Example of femoral components that may be used with the present invention are disclosed in U.S. Pat. Nos. 5,480,453 and 5,326,376 which are both hereby incorporated herein by reference.

When preparing femur 60 to receive the femoral component, the position of the resection removing the femoral ball 62 must be located on femur 60 before performing the resection. In conventional surgical procedures for implanting a prosthetic hip joint which do not employ computer assisted navigation, it is common to expose a substantial portion of the proximal femur so that the surgeon may see or locate by palpation one or more of the major landmarks of the proximal femur such as the center of the femoral ball 62, the greater trochanter 66 and the lesser trochanter. A mechanical measurement device may then be positioned on the exposed femur and aligned with the appropriate anatomical landmarks. The surgeon will have preoperatively determined the desired location of the resection line removing the femoral ball and the location of this line relative to an anatomical landmark. For example, the surgeon may define the location of the resection line by measuring the distance from the line to the lesser trochanter 68 and by determining the angle 61a of the resection line relative to the femoral axis 61. Alternative anatomical landmarks may also be used, for example, the same resection line could be defined by a distance from the center of the femoral ball and by the angle 65a which the line forms with the neck axis 65 defined by femoral neck 64.

The illustrated embodiment is used with a computer assisted navigation system having a display device 76 which may display an image similar to that illustrated in FIG. 3. FIG. 3 also schematically represents a computer assisted navigation system 70 having a position sensor 72 for tracking the movement of reference array 32, a control unit 74 having a processor in addition to display screen 76. In the illustrated embodiment, the display includes a flouroscopy image of femur 60 and a measurement overlay 56. Measurement overlay 56 includes a series of equally spaced parallel lines 58a-58j which are spaced to represent a predefined distance on the actual anatomical structure and thereby form a virtual ruler. For example, the space between each line could represent a distance of 5 mm on the actual anatomical structure. A computer assisted surgical navigation system which overlays a graphical icon representing a surgical instrument on a fluoroscopic image of an anatomical structure and moves the graphical icon to represent the current position of the surgical instrument relative to the anatomical structure is described in the disclosure of U.S. Pat. No. 6,470,207 B1 which is hereby incorporated herein by reference. A similar system which substitutes the graphical image of measurement overlay 56 for the graphical image of the surgical instrument and which repositions measurement overlay 56 to reflect the position and orientation of instrument 20 could be used with the present invention.

As with a conventional hip replacement procedure, a surgeon utilizing the present invention will typically determine a resection location on femoral neck 64 preoperatively and define its location relative to other landmarks on femur 60. For example, the angle 61a formed between a line parallel to the resection line and the femoral axis 61 and the distance from the resection line to the lesser trochanter 68 measured perpendicularly to the resection line may be used to define the location of the resection line. During the surgical procedure, the surgeon will align measurement overlay 54 to reflect these predetermined measurements and then engage projections 50 of instrument 20 with femur 60. Lines 58a-58j may be marked to facilitate this alignment process. For example, line 58e may reflect the position of alignment surface 46 and be marked with a "0". If the spacing of lines is 5 mm, lines 58f, 58g, 58h, 58i, 58j could be marked +5 mm, +10 mm, +15 mm, +20 mm, +25 mm respectively. Similarly, lines 58d through 58a could be marked −5 mm through −20 mm to reflect the relative positions of these lines with respect to surface 46.

Although not shown in FIG. 3, a line representing the position of alignment head 44 and extending perpendicular to lines 58a-58j could be displayed and an angular measurement grid, i.e., a protractor template, could be included in measurement overlay 54 to allow instrument 20 to facilitate the measurement of angles. It would also be possible to provide multiple overlays and allow the surgeon to select a desired overlay.

The surgeon moves instrument 20 to reflect the predetermined resection line location. Movement of instrument 20 may include translation, e.g., repositioning overlay 56 so that line 58c intersects lesser trochanter 68 instead of line 58d, and rotation, e.g., altering the magnitude of angles 65a and 61a. To facilitate the sensing of reference elements 42, array 32 is advantageously positioned so that arms 38a-38d extend horizontally and are positioned vertically above mounting block 28 as shown in FIG. 2. In an optical tracking system, rotation of instrument 20 about the axis defined by handle 22 is generally undesirable and could place array 32 in a position which would prevent its registration in the computer assisted navigation system. After properly positioning instrument 20, femur 60 is marked as described above. Instrument 20 may then be removed and the resection of femoral neck 64 as indicated by mark 54 may be completed using conventional surgical techniques.

Figure 5:
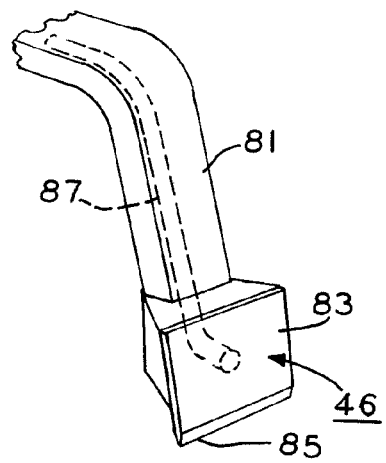
FIG. 5 is a perspective view of an alternative alignment head.

FIG. 5 illustrates another embodiment of the instrument having an alternative alignment head. In the embodiment of FIG. 5, instrument 81 has the same general shape and configuration as instrument 20 and has a reference array 32 mounted thereon. Instrument 81 differs, however, by having an alignment surface which is defined by a plate-shaped electrocautery electrode 83. Electrode 83 has a cauterizing edge 85 which projects outwardly from the alignment head in a manner similar to projections 50 but which defines a continuous edge. Edge 85 has a generally triangular cross section which progressively narrows as it projects outwardly whereby it defines a thin contact line instead of a relative wide band of contact which is the full thickness of electrocautery electrode 83. A conductive member 87 is disposed within instrument 81 and supplies an electric current to electrocautery electrode 83. The current is communicated to the anatomical structure along edge 85.

In the illustrated embodiment, the body of instrument 81, apart from electrode 83 and conductive member 87, may be advantageously formed out of an electrical insulative material such as a plastic or a composite material. In the embodiment shown in FIG. 5, electrocautery electrode 83 defines the entirety of guide surface 46, however, in alternative configurations, electrocautery electrode 83 might define only a portion of alignment surface 46 or be parallel and slightly recessed with respect to surface 46. By disposing electrode 83 on the alignment head, a second instrument is not required to mark the bone when instrument 81 has been properly positioned, instead, cauterizing edge 83 may be used to create the mark on the bone. Conductive material 87 may be a conductive wire which is coupled to a power source located either in instrument 81, such as batteries, or coupled to an exterior power source. Electrocautery electrode 83 functions in a manner similar to conventional electrocautery electrodes which are well known in the art. One example of an instrument having an electrocautery electrode is disclosed in U.S. Pat. No. 5,938,661 the disclosure of which is hereby incorporated herein by reference.

Figure 6:
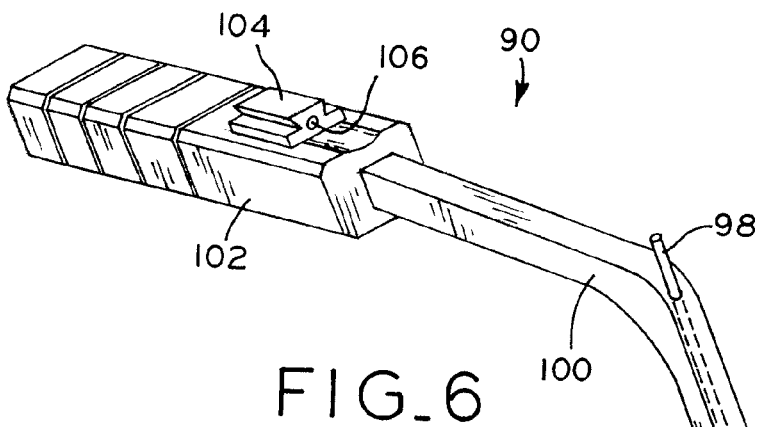
FIG. 6 is a perspective view of another embodiment of an instrument in accordance with the present invention.

FIGS. 6 shows another embodiment of a surgical instrument in accordance with the present invention. An electrocautery electrode 92 is located on the alignment head of instrument 90. Similar to electrode 83, electrode 92 defines an alignment surface. Electrode 92 also defines a plurality of outwardly extending projections 94 similar to projections 50 which form the cauterizing edge of electrode 92. Electrode 92 could also employ alternative edges such as one defining a linear projecting edge similar to edge 83.

Conductive block 96 and conductive rod 98 are in electrical communication with electrocautery electrode 92. Conductive block 96 extends rearwardly of electrode 92 and is encased within the plastic material forming the alignment head of instrument 90. Conductive rod 98 is a rigid rod which extends upwardly from conductive block 96. Except for a short upwardly projecting section, rod 98 is encased within the plastic material forming neck 100. The alignment head of instrument 90 and neck 100 are formed out of a radio-transparent and electrically insulative material such as a plastic material. This allows instrument 90 to be positioned within a fluoroscopic image without neck 100 obscuring the view of the adjacent anatomical structure and also provides electrically insulates conductive block 96 and rod 98.

Electrode 92, and conducting members 96, 98 are all radio-opaque, electrically conductive materials and, thus, will be visible in a fluoroscopic image. In the illustrated embodiment, electrode 92 and conducting members 96, 98 are stainless steel, however, other conductive materials, such as aluminum, may also be used to form electrode 92 and conductive members 96, 98. Grip 102 and dovetail projection 104 are also a radio-opaque, metallic material, e.g., stainless steel, but will generally be sufficiently distant from alignment surface 46 to avoid obscuring the anatomical area of interest. As shown in FIG. 6, grip 102 has a dovetail shaped projection 104 and threaded opening 106 which are used to secure a reference array 32 onto instrument 90.

Figure 7:
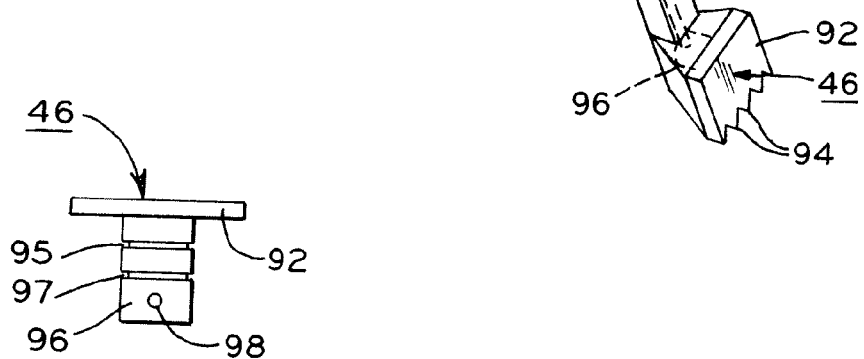
FIG. 7 is a top view of the electrocautery electrode of the instrument shown in FIG. 6.

As best seen in FIG. 7, conductive block 96 includes grooves 95, 97 which encircle the block and can be detected in fluoroscopic images. By using equally spaced grooves, or projection or other visible discontinuities, conductive block 96 provides a measurement function. More specifically, by positioning groove 95 five mm behind alignment surface 46 and groove 97 five mm behind groove 95, these equally spaced grooves can be used to determine the distance of alignment surface 46 from an anatomical landmark, or other detectable object, when viewing a fluoroscopic image of instrument 90 adjacent the anatomical structure.

Although instrument 90 is shown having a mounting feature for reference array 32, by providing member 96 with measurement features, it would be possible to properly position an instrument 90 without an array 32 mounted thereon by viewing a fluoroscopic image without the use of a computer assisted navigational system. The use of electrocautery electrodes 83, 92 may also be used in the absence of a reference array 32 mounted on the instrument and in the absence of fluoroscopic viewable measurement features. Moreover, instrument 20, which does not include an electrocautery electrode or fluoroscopic viewable measurement feature, may also be useful in a conventional surgical procedure in which the placement of instrument 20 is determined without the aid of a computer assisted navigational system.

After guide 90 has been positioned in its proper location, electrocautery electrode 92 is used to mark the bone. By having rigid conducting rod 98 project upwardly out of neck 100, electrical current may be supplied to electrocautory electrode 92 via conducting members 98, 96 by touching the cutting blade, i.e., electrocautery electrode, of a conventional electrocautery device to the projecting length of rod 98.

After resecting femoral neck 64, substantially planar alignment surface 46 may be engaged flush with the bone surface created by the resection to register the position of this surface in the computer assisted navigation system and to verify that the resection was performed at the desired location.

As is known in the art, the relevant dimensional data concerning an anatomical structure of interest, e.g., femur 60, may be determined using data acquired from images of the anatomical structure to generate a data base representing a model of the anatomical structure. The model of the anatomical structure may be a three dimensional model which is developed by acquiring a series of two dimensional images of the anatomical structure. Alternatively, the model of the anatomical structure may be a set of two dimensional images having known spatial relationships or other data structure which can be used to convey information concerning the three dimensional form of the anatomical structure. The model of the anatomical structure may then be used to generate displays of the anatomical structure from various perspectives for preoperative planning purposes and intraoperative navigational purposes. A variety of technologies which may be employed to generate such a model of an anatomical structure are well known in the art and include computed tomography (CT), magnetic resonance imaging (MRI), positron emission tomography (PET), ultrasound scanning and fluoroscopic imaging technologies.

The model of the anatomical structure obtained by such imaging technologies can be used for the intraoperative guidance of a surgical instrument by facilitating the determination and display of the relative position and orientation of the surgical instrument with respect to the actual anatomical structure. For example, if the model of the anatomical structure is a set of two dimensional images having known spatial relationships, several such images may be simultaneously displayed during the surgical procedure. By also displaying the position of the instrument in the images and displaying images taken from different perspectives, e.g., one image facilitating the display of instrument movement along the x and y coordinate axes and another image facilitating the display instrument movement along the z axis, the individual images may together represent the movement of the instrument in three dimensions. The illustrated embodiment of the present invention may be utilized without displaying movement of instrument 20 in all three dimensions.

For reference purposes, a coordinate system defined by the actual anatomical structure which is the subject of interest will be referred to herein as the anatomical coordinate system and a coordinate system defined by the model of the anatomical structure will be referred to as the image coordinate system. Data concerning the fixed size and shape of the surgical instrument, or of a relevant portion thereof, which will be used in the image guided procedure is also determined preoperatively to obtain a three dimensional model of the instrument or the relevant portions thereof.

Rigid anatomical structures, such as skeletal elements, are well suited for such image guided surgical techniques and individual skeletal elements may be used to define separate coordinate systems. The different rigid structures, e.g., skeletal elements, may be subject to relative movement, for example, the femur and acetabulum of a patient may be relatively moved during the surgical procedure and separate three dimensional models and coordinate systems may be created for the different skeletal elements. For example, during a hip replacement procedure, a three dimensional model of the femur defining a first coordinate system may be utilized during the resection of the femur while a separate coordinate system defined by a three dimension model of the pelvis is utilized during the preparation of the acetabulum.

When using computer assisted navigation, also referred to as computer implemented image guidance, to conduct a surgical technique, the image coordinate system is registered with the anatomical coordinate system and the position of the surgical instrument is also registered within the image coordinate system. After the registration of both the actual anatomical structure and the surgical instrument, the relative position and orientation of the surgical instrument may be communicated to the surgeon by displaying together images of the anatomical structure and instrument based upon the three dimensional models of the anatomical structure and instrument which were previously acquired. In FIG. 3 illustrating an embodiment of the present invention, instrument 20 is not displayed, instead a measurement overlay 54 is displayed in combination with a fluoroscopy image of femur 60. Overlay 54 is moved to reflect changes in the position of instrument 20 after registering the location of instrument 20 and femur 60 in computer assisted navigation system 70. In an alternative embodiment of the present invention, an image of instrument 20 could also be displayed with measurement overlay 54.

Computer implemented image guidance systems which provide for the registration of an actual anatomical structure with a three dimensional model representing that structure together with the registration or localization of a surgical instrument within the image coordinate system to facilitate the display of the relative positions of the surgical instrument and the actual anatomical structure are known in the art. Known methods of registering the anatomical structure with the image coordinate system include the use of implanted fiducial markers which are recognizable by one or more scanning technologies. Alternatively, implants which may be located by physically positioning a digitizing probe or similar device in contact or at a known orientation with respect to the implant. Instead of using implants, it may also be possible to register the two coordinate systems by aligning anatomical landmark features. U.S. Pat. Nos. 6,236,875 B1 and 6,167,145 both describe methods of registering multiple rigid bodies and displaying the relative positions thereof and the disclosures of both of these patents are hereby incorporated herein by reference.

Tracking devices employing various technologies enabling the registration or localization of a surgical instrument and the tracking of the instrument motion with respect to the anatomical coordinate system, which has been registered with the image coordinate system, are also known. For example, optical tracking systems which detect light from reflected or emitted by reflective targets or localizing emitters secured in a known orientation to the instrument are known for determining the position of a surgical instrument and registering the position of the instrument within an image coordinate system representing a three dimensional model of an anatomical structure. For example, such a tracking system may take the form of a sensor unit having one or more lenses each focusing on separate charge coupled device (CCD) sensitive to infrared light. The sensor unit detects infrared light emitted by three or more non-linearly positioned light emitting diodes (LEDs) secured relative to the instrument. A processor analyzes the images captured by the sensor unit and calculates the position and orientation of the instrument. By registering the position of the sensing unit within the image coordinate system, the position of the instrument relative to the anatomical structure, which has also been registered with the image coordinate system, may be determined and tracked as the instrument is moved relative to the anatomical structure.

Alternative localizing systems may employ localizing emitters which emit an electromagnetic signal in the radio frequency or which emit visible light. Other types of localizing systems that could be used with the present invention employ referencing elements or other distinguishing elements which are radio-opaque. It is also possible to employ digitizing physical probes which are brought into physical contact with the instrument at predefined locations on the instrument to register the position of the instrument.

In the disclosed embodiment, the localizing system includes a light source and reference elements 42 reflect the light. The localizing system then detects the reflected light and computes the location of the individual reference elements 42 in a known manner. Reference elements 42 may be obtained from Northern Digital Inc. having a place of business at 103 Randall Dr., Waterloo, Ontario, Canada, N2V1C5. Northern Digital Inc. supplies image guidance systems under the brand names Optotrak® and Polaris® which may be used with the present invention. The present invention may also be used with other computer assisted navigation systems such as those described above or otherwise known in the art. For example, Medtronic, Inc. headquartered in Minneapolis, Minn. manufactures and sells various computer assisted surgical navigation systems under the trademark StealthStation® such as the FluoroNav™ Virtual Fluoroscopy System which could also be adapted for use with the present invention.

Figure 4:
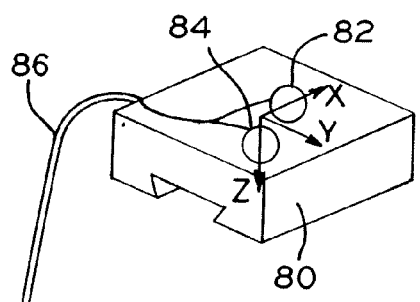
FIG. 4 is a schematic view of an alternative reference structure which may be used with the present invention.

The use of a removably mountable reference array 32 facilitates the use of instrument 20 with alternative types of computer assisted navigational systems by allowing different reference arrays having alternative referencing elements to be mounted on a single instrument body design. For example, an alternative embodiment of the present invention could be employed with a computer assisted navigation system which utilizes magnetic fields instead of optical tracking to determine the position and orientation of the tracked instrument. FIG. 4 schematically illustrates an alternative reference structure 80 which may be used with instrument 20 in such a system. Reference structure 80 has referencing elements formed by mutually perpendicular wire loops 82 and 84 which are in communication with the processor of the computer assisted navigation system via communications cable 86. Wireless communication between wire loops 82 and 84 and the processor of the computer assisted navigation system using radio signals could also be employed. In such a system, a field generator would be used to generate an electromagnetic field and wire loops 82 and 84 would function as field sensors. With the sensor data provided by a plurality of mutually perpendicular field sensors, the system could calculate the position and orientation of instrument 20 on which reference member 80 is mounted. Reference structure 80 includes a dovetail connection and is mounted to instrument 20 in the same manner as reference array 32. Alternatively, a single field sensor could be employed to sense a plurality of field generators located at different positions to define the location and orientation of the single field sensor. The positions of wire loops 82 and 84 are fixed relative to reference member 80. To form reference structure 80, a polymeric material may encase one or more copper wire coils. If more than one coil is used, such as illustrated in FIG. 4, they are advantageously positioned at a mutually perpendicular orientation. In the embodiment illustrated in FIG. 4, two substantially cylindrical wire coils are located such that the axes of the coils are aligned with the X and Z axes of a Cartesian coordinate system, a third mutually perpendicular loop could be positioned to have its axis correspond to the Y axis.

A variety of referencing elements which are used with magnetic fields which could be adapted for use with instrument 20 are known in the art. For example, known systems using magnetic fields to determine the position and orientation of a surgical instrument or other body are described by U.S. Pat. Nos. 5,913,820; 6,381,485 B1; 6,402,762 B2; 6,474,341 B1; 6,493,573 B1; and 6,499,488 B1 the disclosures of these patents are all hereby incorporated herein by reference.

The present invention may be used in a surgical procedure for implanting a prosthetic hip joint which employs, during other aspects of the procedure, instruments described by McGinley et al. in a U.S. Patent Application entitled GUIDANCE SYSTEM FOR ROTARY SURGICAL INSTRUMENT having attorney docket no. ZIM0165 filed on the same date as the present application, and by Grimm et al. in a U.S. Patent Application entitled IMPLANT REGISTRATION DEVICE FOR SURGICAL NAVIGATION SYSTEM having attorney docket no. ZIM0166 filed on the same date as the present application, the disclosures of both of these applications are hereby incorporated herein by reference.

While this invention has been described as having an exemplary design, the present invention may be further modified within the spirit and scope of this disclosure. This application is therefore intended to cover any variations, uses, or adaptations of the invention using its general principles.

What is claimed is:

1. A surgical instrument for determining a location on an anatomical structure in cooperation with a computer assisted navigation system, said surgical instrument comprising:
a grip portion;
a reference structure disposed on said instrument, said reference structure having at least one reference element registerable in the computer assisted navigation system; and
an alignment head having a substantially planar alignment surface and a plurality of outwardly extending projections disposed along an edge of said alignment surface, each of said plurality of outwardly extending projections having a longitudinal axis, said plurality of outwardly extending projections extending parallel to said alignment surface, wherein said longitudinal axes of said plurality of outwardly extending projections are parallel to said alignment surface, and wherein said projections are engageable with the anatomical structure and said alignment surface provides a guide for making a mark on the anatomical structure.

2. The surgical instrument of claim 1 wherein said instrument forms a rigid elongate body between said at least one reference element and said alignment head.

3. The surgical instrument of claim 1 wherein said at least one reference element is removably mounted on said surgical instrument.

4. The surgical instrument of claim 1 wherein said projections each include a surface disposed substantially co-planar with said alignment surface.

5. The surgical instrument of claim 1 wherein said at least one reference element comprises at least three non-linearly positioned reference elements.

6. The surgical instrument of claim 1 wherein said at least one reference element comprises an electromagnetic field sensor.

7. The surgical instrument of claim 1 wherein said at least one reference element comprises a light reflective structure.

8. A surgical instrument for facilitating marking a location on an anatomical structure and for use with a computer assisted surgery system, the instrument comprising:
a grip portion;
a reference structure disposed on the instrument, said reference structure having at least one reference element registerable in the computer assisted surgery system; and
an alignment device attached to said reference structure, said alignment device including at least one substantially planar serrated edge having a plurality of outwardly extending projections and a substantially planar surface, each of said plurality of outwardly extending projections having a longitudinal axis, said plurality of outwardly extending projections of said serrated edge extending from said planar surface, wherein said longitudinal axes of said plurality of outwardly extending projections are parallel to said planar surface.

9. The surgical instrument of claim 8, wherein the surgical instrument forms a rigid elongate body between said at least one reference element and said alignment device.

10. The surgical instrument of claim 8, wherein said at least one reference element is removably mounted on the surgical instrument.

11. The surgical instrument of claim 8, wherein said serrated edge includes a surface disposed substantially co-planar with said planar surface.

12. The surgical instrument of claim 8, wherein said at least one reference element comprises at least three non-linearly positioned reference elements.

13. The surgical instrument of claim 8, wherein said at least one reference element comprises an electromagnetic field sensor.

14. The surgical instrument of claim 8, wherein said at least one reference element comprises a light reflective structure.

15. An osteotomy guide for marking a location on an anatomical structure and for use with a computer assisted surgery system, the guide comprising:
  a grip portion;
  a reference structure connected to said grip portion, said reference structure having at least one reference element registerable in the computer assisted surgery system; and
  a marking guide including a substantially planar surface and a plurality of outwardly extending projections disposed along at least one edge of said substantially planar surface, each of the plurality of outwardly extending projections having a longitudinal axis, said longitudinal axes of each of said outwardly extending projections extending substantially coplanar with said surface.

16. The osteotomy guide of claim 15, wherein the osteotomy guide forms a rigid elongate body between said at least one reference element and said marking guide.

17. The osteotomy guide of claim 15, wherein said at least one reference element is removably mounted on the osteotomy guide.

18. The osteotomy guide of claim 15, wherein said at least one reference element comprises at least three non-linearly positioned reference elements.

19. The osteotomy guide of claim 15, wherein said at least one reference element comprises an electromagnetic field sensor.

20. The osteotomy guide of claim 15, wherein said at least one reference element comprises a light reflective structure.

* * * * *